United States Patent
Kubo et al.

(10) Patent No.: US 9,833,594 B2
(45) Date of Patent: Dec. 5, 2017

(54) BALLOON CATHETER

(71) Applicant: ASAHI INTECC CO., LTD., Nagoya-shi, Aichi (JP)

(72) Inventors: Yuta Kubo, Seto (JP); Michihiro Ikegaya, Nagoya (JP); Yoshiki Kaneko, Nishio (JP)

(73) Assignee: ASAHI INTECC CO., LTD., Nagoya-shi (JP)

( * ) Notice: Subject to any disclaimer, the term of this patent is extended or adjusted under 35 U.S.C. 154(b) by 161 days.

(21) Appl. No.: 14/606,455

(22) Filed: Jan. 27, 2015

(65) Prior Publication Data

US 2015/0231375 A1    Aug. 20, 2015

(30) Foreign Application Priority Data

Feb. 20, 2014    (JP) ................... 2014-030221

(51) Int. Cl.
*A61M 25/00*    (2006.01)
*A61M 25/10*    (2013.01)

(52) U.S. Cl.
CPC ...... *A61M 25/005* (2013.01); *A61M 25/0067* (2013.01); *A61M 25/0068* (2013.01);
(Continued)

(58) Field of Classification Search
CPC ............ A61M 25/0045; A61M 25/005; A61M 25/0053; A61M 25/0054; A61M 25/0069;
(Continued)

(56) References Cited

U.S. PATENT DOCUMENTS

| 5,533,988 A | 7/1996 | Dickerson et al. |
| 5,743,874 A * | 4/1998 | Fischell ........... A61F 2/95 604/103.04 |

(Continued)

FOREIGN PATENT DOCUMENTS

| JP | 2003-517898 A | 6/2003 |
| JP | 2005-160536 A | 6/2005 |

OTHER PUBLICATIONS

Aug. 13, 2015 Extended European Search Report issued in European Application No. 15154085.3.
(Continued)

*Primary Examiner* — Kevin C Sirmons
*Assistant Examiner* — Shefali Patel
(74) *Attorney, Agent, or Firm* — Oliff PLC

(57) ABSTRACT

A balloon catheter having a distal-end tip which, even if caught in a stenosis, will not break apart from a distal end of an inner shaft of the balloon catheter when the balloon catheter is forcibly rotated or pulled by an operator. The distal-end tip of the balloon catheter is fixed to the distal end of the inner shaft, and a connecting tube covers an outer surface of the distal end of the inner shaft and a proximal end of the distal-end tip. An inwardly protruding portion of the connecting tube is embedded into the distal-end tip. This creates an anchoring effect and increases a welding area between an outer surface of the distal-end tip and an inner surface of the connecting tube, thereby reducing a risk that the distal-end tip will break apart from the distal end of the inner shaft.

11 Claims, 6 Drawing Sheets

(52) U.S. Cl.
CPC ........ *A61M 25/0069* (2013.01); *A61M 25/10* (2013.01); *A61M 25/0026* (2013.01); *A61M 25/1025* (2013.01); *A61M 2025/0037* (2013.01); *A61M 2025/1081* (2013.01); *A61M 2025/1093* (2013.01)

(58) Field of Classification Search
CPC ...... A61M 2025/0081; A61M 25/1025; A61M 2025/1093; A61M 25/0067; A61M 25/0068; A61M 25/008; A61M 25/10; A61M 2025/1081
See application file for complete search history.

(56) References Cited

U.S. PATENT DOCUMENTS

| | | | |
|---|---|---|---|
| 5,762,637 A | 6/1998 | Berg et al. | |
| 6,010,521 A | 1/2000 | Lee et al. | |
| 6,368,301 B1 * | 4/2002 | Hamilton | A61M 25/0069 604/103 |
| 6,837,869 B2 | 1/2005 | Hamilton et al. | |
| 6,918,920 B1 | 7/2005 | Wang et al. | |
| 7,465,311 B2 | 12/2008 | Wang et al. | |
| 8,221,444 B2 | 7/2012 | Wang et al. | |
| 2002/0082550 A1 | 6/2002 | Hamilton et al. | |
| 2003/0032921 A1 | 2/2003 | Duchamp | |
| 2006/0142733 A1 | 6/2006 | Forsberg | |
| 2014/0025045 A1 | 1/2014 | Abt et al. | |

OTHER PUBLICATIONS

Jan. 28, 2016 Notification of Reasons for Refusal issued in Japanese Patent Application No. 2014-030221.
Aug. 21, 2017 Office Action issued in Chinese Patent Application No. 201510041230.7.

* cited by examiner

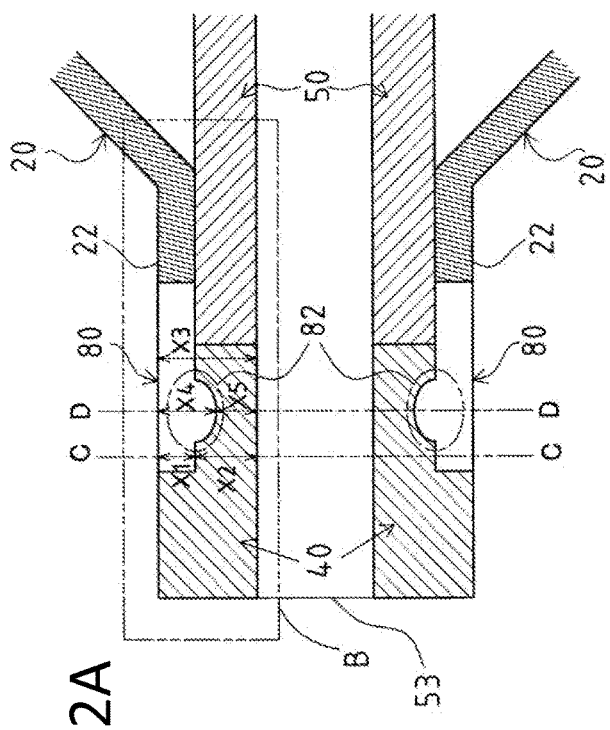
FIG. 2A
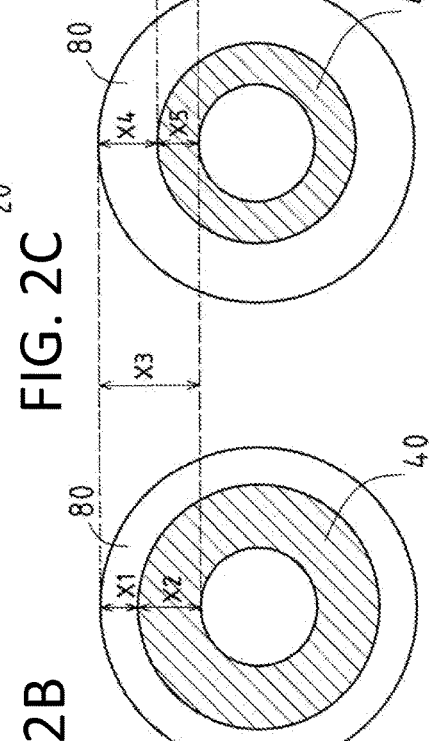
FIG. 2B
FIG. 2C
FIG. 2D

BALLOON CATHETER

CROSS-REFERENCE TO RELATED APPLICATION

This application claims priority to Japanese Application No. 2014-030221 filed on Feb. 20, 2014, the contents of which are incorporated by reference herein in their entirety.

BACKGROUND

The disclosed embodiments relate to a medical device. Specifically, the disclosed embodiments relate to a balloon catheter to be inserted into a stenosis formed in a blood vessel in order to enlarge the stenosis and restore blood flow.

Conventionally, balloon catheters are widely used as therapeutic catheters for enlarging stenoses formed in blood vessels by inserting the balloon catheter into the stenosis. A balloon catheter mainly includes a balloon acting as an inflating body, an outer shaft welded to the proximal end of the balloon, and an inner shaft inserted into the balloon and the outer shaft. The inner shaft is used for inserting a guide wire. An inflation lumen provided between the outer shaft and the inner shaft is used for passing a liquid (e.g., a contrast medium and a physiological saline) for inflating the balloon.

The distal end of the inner shaft has a distal-end tip made of a soft resin. Thus, even if an operator presses the balloon catheter in a distal direction so as to hit a blood vessel wall with the distal end of the balloon catheter, the balloon catheter hardly damages the blood vessel wall.

However, when the balloon catheter having a soft distal-end tip is inserted into a stenosis, the soft distal-end tip may become caught in the stenosis. If the balloon catheter is forcibly rotated or pulled by an operator while the distal-end tip is caught in the stenosis, the distal-end tip cannot be removed from the stenosis and may break apart from the inner shaft. As a solution to this problem, U.S. Pat. No. 6,918,920 describes a balloon catheter having a connecting tube that covers the distal end of the inner shaft and the rear end of the distal-end tip from the outside.

In the balloon catheter of U.S. Pat. No. 6,918,920, however, when a distal-end tip having a short length is used, a welding area between the outer surface of the distal-end tip and the inner surface of the connecting tube is small. Unfortunately, this reduces the welding strength between the distal-end tip, and the connecting tube and thus the distal-end tip caught in the stenosis may still break apart from the distal end of the inner shaft when the balloon catheter is forcibly rotated or pulled by an operator.

SUMMARY

The disclosed embodiments have been devised in view of the above-discussed circumstances. An object of the disclosed embodiments is to provide a balloon catheter in which an inwardly protruding portion of a connecting tube is embedded into a distal-end tip, thereby increasing an anchoring effect and a welding area between the outer surface of the distal-end tip and the inner surface of the connecting tube. Thus, even if the distal-end tip becomes caught in a stenosis, the distal-end tip will not break apart from the distal end of the balloon catheter's inner shaft when the balloon catheter is forcibly rotated or pulled by an operator.

The problem is addressed by the following solutions:

A balloon catheter of the disclosed embodiments includes a balloon, an inner shaft fixed to a distal end of the balloon, a distal-end tip fixed to a distal end of the inner shaft, and a connecting tube covering an outer surface on the distal end of the inner shaft and a proximal end of the distal-end tip, wherein the connecting tube has an inwardly protruding portion that is embedded into the distal-end tip.

In the disclosed balloon catheter, the connecting tube may be made of a resin having a greater stiffness than the distal-end tip and a lower stiffness than the inner shaft. Furthermore, the inwardly protruding portion of the connecting tube may be in contact with the distal end of the inner shaft. A proximal end of the connecting tube may cover the distal end of the balloon.

As described above, the connecting tube has an inwardly protruding portion that is embedded into the distal-end tip. Thus, even if the distal-end tip is caught in a stenosis, the anchoring effect of the inwardly protruding portion of the connecting tube reduces the risk that the distal-end tip will break apart from the inner shaft. Moreover, the thick portion of the connecting tube increases a welding area between the outer surface of the distal-end tip and the inner surface of the connecting tube. Even if the distal-end tip has a short length, the risk that the distal-end tip will break apart from the inner shaft is minimized.

The connecting tube may be made of a resin having a greater stiffness than the distal-end tip and a lower stiffness than the inner shaft. This reduces the difference in stiffness between the distal end of the inner shaft and the proximal end of the distal-end tip. Thus, there is hardly any concentration of tensile stress formed between the distal end of the inner shaft and the proximal end of the distal-end tip even when the balloon catheter is inserted into a curved blood vessel. Moreover, the inwardly protruding portion of the connecting tube having a medium stiffness suppresses the generation of tensile stress in a distal direction. This can reduce the risk that the distal-end tip will break apart from the distal end of the inner shaft when caught in a stenosis.

The inwardly protruding portion of the connecting tube may be in contact with the distal end of the inner shaft. Thus, when an operator applies a pressing force in the distal direction of the balloon catheter, the pressing force is gradually transmitted from the inner shaft to the distal-end tip through the inwardly protruding portion of the connecting tube. This can improve the pressing force of the balloon catheter.

The proximal end of the connecting tube may extend to and cover the distal end of the balloon. This reduces the possibility that the balloon will detach from the inner shaft when a high pressure is applied to the balloon.

BRIEF DESCRIPTION OF THE DRAWINGS

FIG. 2A is an enlarged view of part A of FIG. 1, FIG. 2B is a cross-sectional view taken along line C-C of FIG. 2A, FIG. 2C is a cross-sectional view taken along line D-D of FIG. 2A, and FIG. 2D is a modification of FIG. 2B.

DETAILED DESCRIPTION OF EMBODIMENTS

Figure 1:
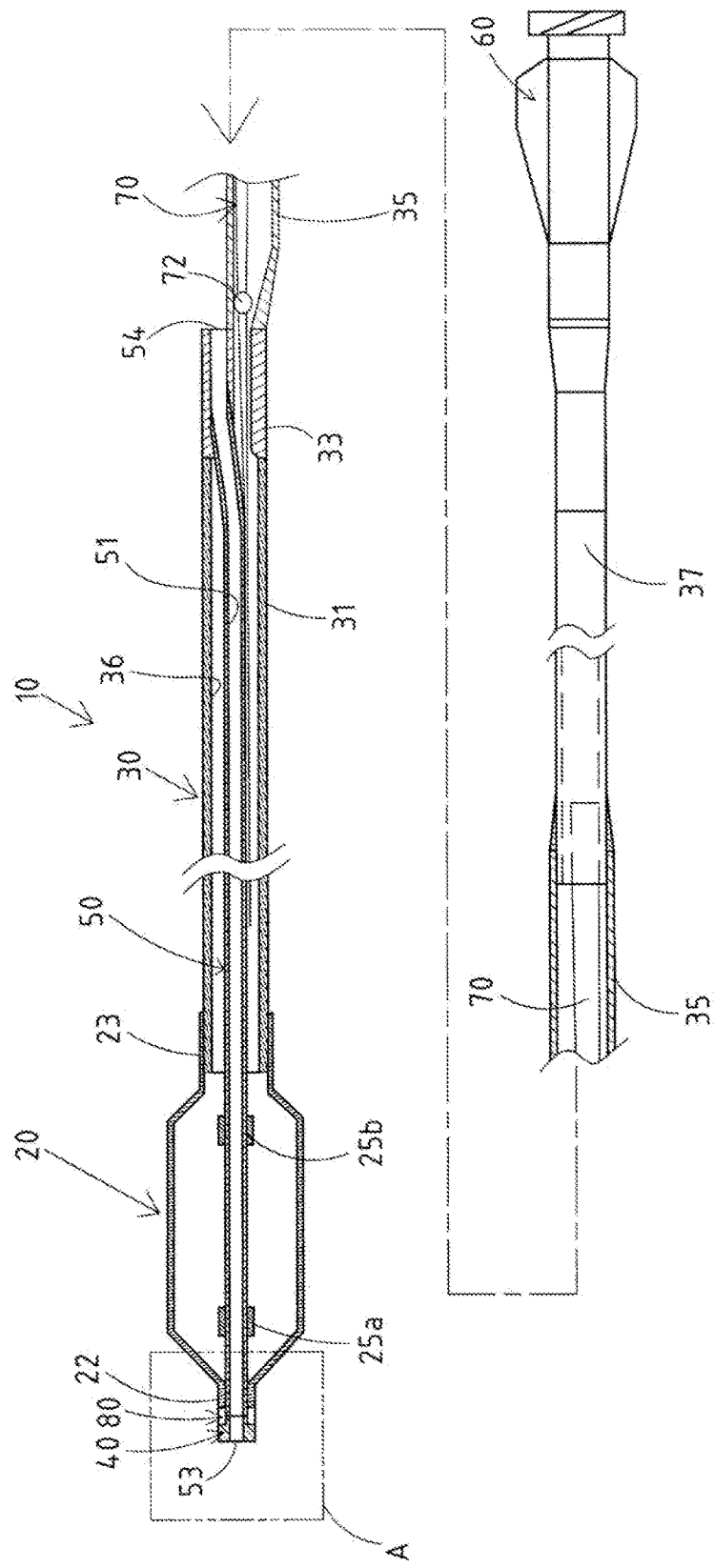
FIG. 1 is an overall view of a balloon catheter according to the disclosed embodiments.

A balloon catheter 10 according to the disclosed embodiments will be described in the following example with reference to FIGS. 1 to 2D. In FIGS. 1 and 2A, the left side indicates a distal end to be inserted into a body, while the right side indicates a proximal end to be operated by an operator, e.g., a doctor.

For example, the balloon catheter 10 may be used for enlarging and treating a stenosis formed in a heart vessel. As shown in FIG. 1, the balloon catheter 10 mainly includes a balloon 20, an outer shaft 30, a distal-end tip 40, an inner shaft 50, a connector 60, a reinforcing member 70, and a connecting tube 80.

The balloon 20 for enlarging a stenosis is a resin member including a distal-end attachment part 22 at the distal end and a proximal-end attachment part 23 at the proximal end. The distal-end attachment part 22 is welded (fixed) to the distal end of the inner shaft 50 and the proximal end of the connecting tube 80, while the proximal-end attachment part 23 is welded (fixed) to the distal end of the outer shaft 30. In FIG. 1, although the proximal-end attachment part 23 is welded to the outer surface of the distal end of the outer shaft 30, the disclosed embodiments are not limited to this configuration. The proximal-end attachment part 23 may instead be welded to the inner surface of the distal end of the outer shaft 30.

The outer shaft 30 is a cylindrical member constituting an inflation lumen 36 for supplying a liquid, such as a contrast medium and a physiological saline, to inflate the balloon 20. The outer shaft 30 includes, from the distal end, a distal-end outer shaft 31, a guide wire port 33, an intermediate outer shaft 35, and a proximal-end outer shaft 37. The distal-end outer shaft 31 and the intermediate outer shaft 35 are tubes made of resins such as a polyamide, polyamide elastomer, polyolefin, polyester, or polyester elastomer. The guide wire port 33 is a welded part of the distal-end outer shaft 31, the intermediate outer shaft 35, and the inner shaft 50.

The inner shaft 50 is inserted into the distal-end outer shaft 31. The inflation lumen 36 is formed between the distal-end outer shaft 31 and the inner shaft 50.

The proximal-end outer shaft 37 is a metallic cylindrical member that is called a hypotube. The distal end of the proximal-end outer shaft 37 is inserted into the proximal end of the intermediate outer shaft 35 and is welded therein. A connector 60 is attached to the proximal end of the proximal-end outer shaft 37. When a liquid such as a contrast medium and a physiological saline is supplied to inflate the balloon 20 from an indeflator (not shown) attachable to the connector 60, the liquid passes through the inflation lumen 36 and inflates the balloon 20. The material of the proximal-end outer shaft 37 is not particularly limited. The proximal-end outer shaft 37 may be made of a superelastic alloy such as stainless steel (SUS304) or a Ni—Ti alloy.

The inner shaft 50 forms a guide wire lumen 51 in which a guide wire can be inserted. The proximal end of the inner shaft 50 is joined to the guide wire port 33 of the outer shaft 30 to form a proximal-end guide wire port 54.

As will be described later, the distal-end tip 40 is welded to the distal end of the inner shaft 50. The distal-end tip 40 is made of a soft resin. The material is not particularly limited, and materials such as polyurethane or a polyurethane elastomer may be used. The distal-end tip 40 has a distal-end guide wire port 53 on the distal end.

The inner shaft 50 includes radio-opaque markers 25a and 25b that are attached in the balloon 20 to locate the balloon 20 under radiation exposure. The number and locations of the markers 25a and 25b can be optionally changed according to the length of the balloon 20.

The reinforcing member 70 is attached to the inner surface of the distal end of the proximal-end outer shaft 37. The reinforcing member 70 is circular in cross section and is a tapered metallic wire rod that decreases in diameter toward the distal end of the reinforcing member 70. The material of the reinforcing member 70 is not particularly limited. For example, the reinforcing member 70 may be made of a superelastic alloy such as stainless steel (SUS304) or a Ni—Ti alloy. The reinforcing member 70 passes through the intermediate outer shaft 35 and the guide wire port 33 and then extends to the distal-end outer shaft 31.

The reinforcing member 70 has a pressing part 72 positioned near the junction between the intermediate outer shaft 35 and the guide wire port 33. When an operator applies a pressing force in the distal direction of the balloon catheter 10, the pressing part 72 contacts the guide wire port 33 and transmits the pressing force from the guide wire port 33 to the outer shaft 30 and the inner shaft 50. The pressing part 72 is preferably made of the same material as the reinforcing member 70.

FIG. 2A is an enlarged view of part A of FIG. 1. The distal-end attachment part 22 of the balloon 20 is welded to the distal end of the inner shaft 50. The connecting tube 80 covers the distal end of the inner shaft 50 and the proximal end of the distal-end tip 40 from the outside. The connecting tube 80 has a thick portion 82 (inwardly protruding portion) embedded into the distal-end tip 40.

FIG. 2B is a cross-sectional view taken along line C-C of FIG. 2A. FIG. 2C is a cross-sectional view taken along line D-D of FIG. 2A. In FIG. 2B, X1 denotes the thickness of the connecting tube 80 other than at the thick portion 82, and X2 denotes the thickness of the distal-end tip 40 at a corresponding position. In FIG. 2C, X4 denotes the thickness of the connecting tube 80 at the thick portion 82, and X5 denotes the thickness of the front-end tip 40 at a corresponding position. In both FIGS. 2B and 2C, X3 denotes the sum of the thickness of the connecting tube 80 and the thickness of the distal-end tip 40. The sum X3 of the thickness of the connecting tube 80 and the thickness of the distal-end tip 40 is constant in the longitudinal direction. In other words, X1+X2=X4+X5=X3. Thus, at the thick portion 82, the distal-end tip 40 has a smaller thickness (X5<X2) and the connecting tube 80 has a larger thickness (X4>X1) than at a portion other than the thick portion 82.

The thick portion 82 of the connecting tube 80 is embedded into the distal-end tip 40. Thus, even if the distal-end tip 40 becomes caught in a stenosis, the anchoring effect of the thick portion 82 of the connecting tube 80 will reduce the risk that the distal-end tip 40 will break apart from the distal end of the inner shaft 50. Moreover, the thick portion 82 of the connecting tube 80 increases a welding area between the outer surface of the distal-end tip 40 and the inner surface of the connecting tube 80. Even if the distal-end tip 40 has a short length, the risk that the distal-end tip 40 will break apart from the distal end of the inner shaft 50 will be reduced.

In FIGS. 2A and 2C, the thick portion 82 of the connecting tube 80 protrudes inwardly along an entire inner circumference of the connecting tube 80. However, the disclosed embodiments are not limited to this configuration.

Figure 6A:
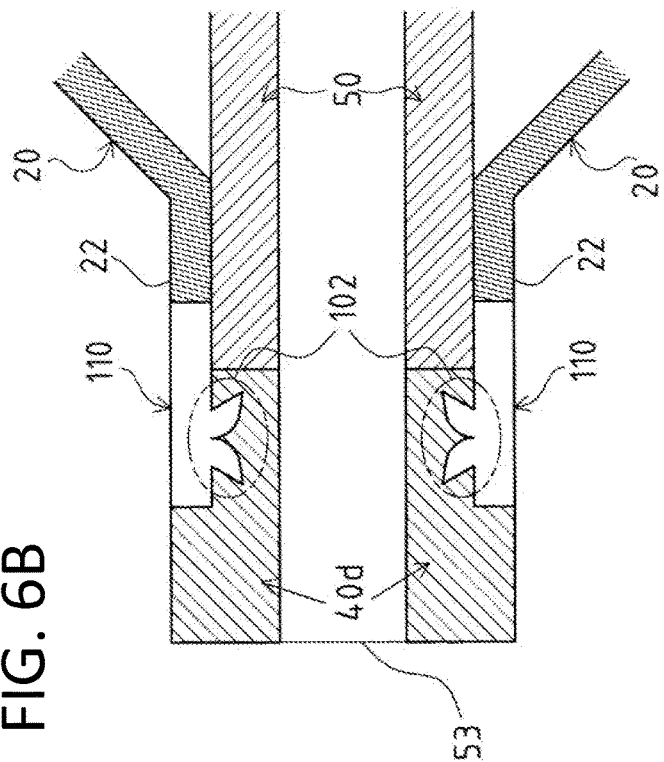
FIGS. 6A and 6B show modifications of FIG. 2A.
Figure 6B:
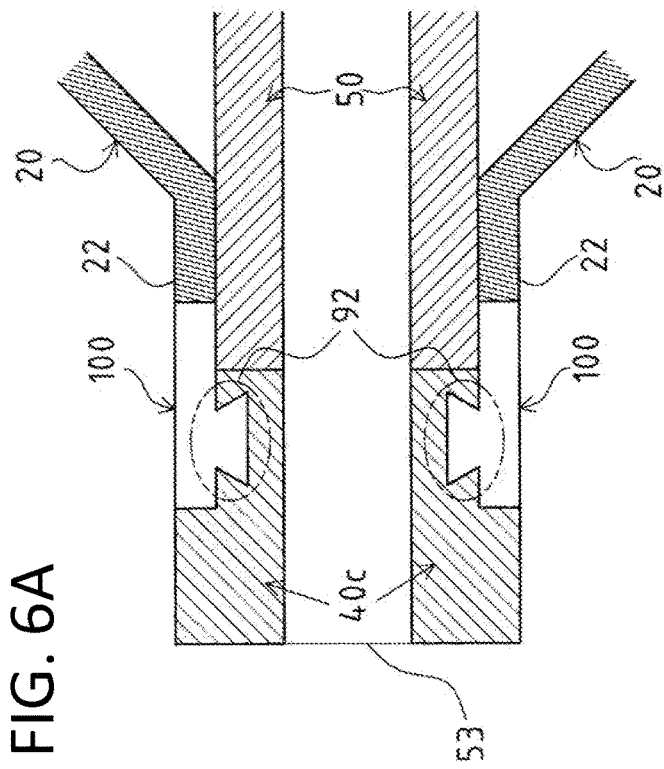

For example, as shown in FIG. 2D, thick portions 82a may be provided at only certain portions of the connecting tube 80a. In FIG. 2D, the two thick portions 82a are embedded into a distal-end tip 40a. The number of thick portions 82a may be optionally adjusted. Moreover, the shapes of the thick portions 82 and 82a are not particularly limited and thus may be shaped like thick portions 92 and 102 shown in FIGS. 6A and 6B. In FIG. 6A, a thick portion 92 of a connecting tube 100 is embedded into a distal-end tip 40c. In FIG. 6B, a thick portion 102 of a connecting tube 110 is embedded into a distal-end tip 40d. Thus, even if the distal-end tips 40c and 40d are caught in a stenosis, the anchoring effect of the thick portions 92 and 102 will reduce the risk that the front-end tips 40c and 40d will break apart from the distal end of the inner shaft 50.

In the above explanation, the thick portions 82, 82a, 92, and 102 protrude longitudinally into the distal-end tips 40, 40a, 40c, and 40d, respectively. Each of the thick portions 82, 82a, 92, and 102 may be replaced with multiple thick portions longitudinally provided on each of the distal-end tips. The provision of the multiple thick portions 82, 82a, 92, 102 in the longitudinal direction can increase the anchoring effect and the welding areas between the distal-end tips 40, 40a, 40c, and 40d and the connecting tubes 80, 80a, 100, and 110, thereby preventing the distal-end tips 40, 40a, 40c, and 40d from breaking apart from the distal end of the inner shaft 50.

Figure 3:
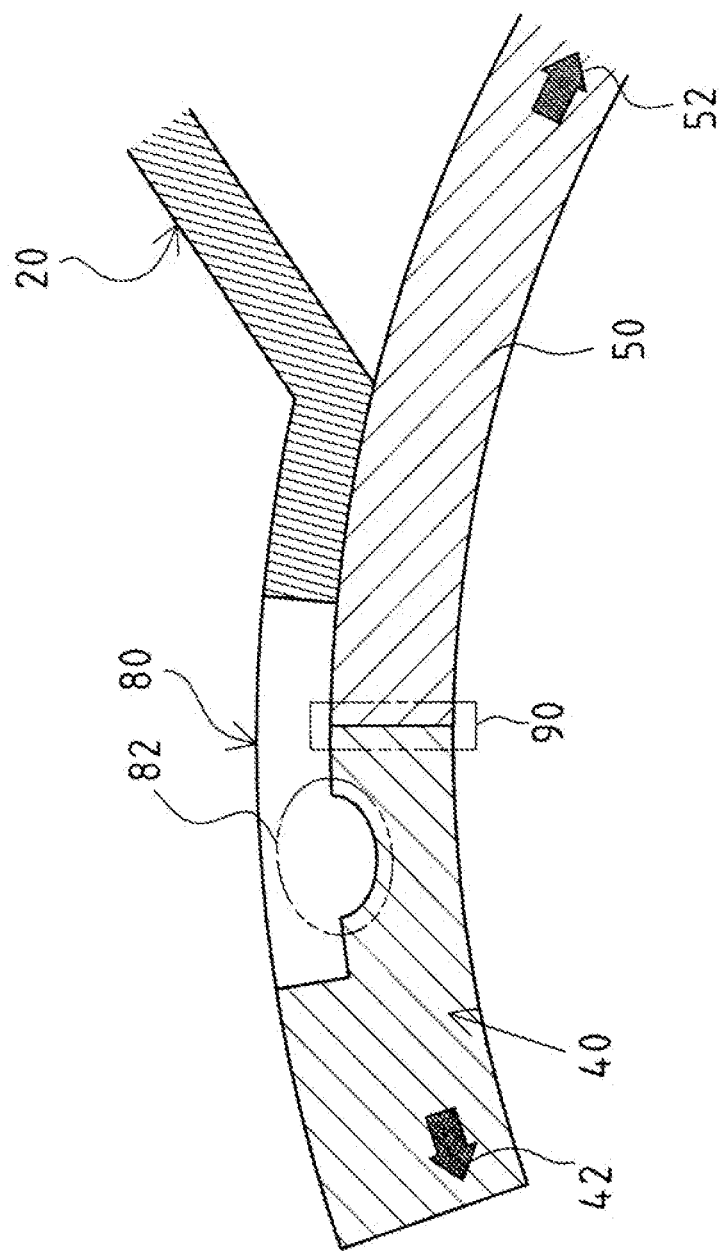
FIG. 3 is an enlarged view of part B of FIG. 2A, illustrating a state of the balloon catheter inserted into a curved blood vessel.

FIG. 3 shows the balloon catheter 10 inserted into a curved blood vessel. For illustration, FIG. 3 only shows an enlarged view of part B of FIG. 2A.

When the balloon catheter 10 is inserted into the curved blood vessel, a tensile stress 42 is generated in the distal-end tip in a distal direction along the curved blood vessel; meanwhile, a tensile stress 52 is generated in the inner shaft in a proximal direction along the curved blood vessel. Thus, a difference in stiffness at a boundary 90 between the proximal end of the distal-end tip 40 and the distal end of the inner shaft 50 may establish a stress concentration at the boundary 90. This may break the distal-end tip 40 apart from the distal end of the inner shaft 50. If a soft resin were used for both the inner shaft 50 and the distal-end tip 40 in order to reduce the difference in stiffness at the boundary 90 between the proximal end of the distal-end tip 40 and the distal end of the inner shaft 50, it would be difficult to transmit the operator's pressing force to the distal-end tip 40, leading to difficulty in inserting the balloon catheter into the stenosis.

Hence, in the balloon catheter 10, the connecting tube 80 covering an outer surface on the proximal end of the distal-end tip 40 and the distal end of the inner shaft 50 is made of a resin having a greater stiffness than the distal-end tip 40 and a lower stiffness than the inner shaft 50. The inner shaft 50 made of a resin having high stiffness allows efficient transmission of a pressing force of an operator to the distal-end tip 40 through the inner shaft 50. Furthermore, the connecting tube 80 made of a resin having a medium stiffness can reduce a difference in stiffness at the boundary 90 between the proximal end of the distal-end tip 40 and the distal end of the inner shaft 50. Thus, a stress concentration is not formed at the boundary 90 between the proximal end of the distal-end tip 40 and the distal end of the inner shaft 50 when the balloon catheter 10 is inserted into the curved blood vessel, and the likelihood that the distal-end tip 40 will break apart from the distal end of the inner shaft 50 is reduced. The thick portion 82 of the connecting tube 80 having a medium stiffness can suppress the tensile stress 42 generated in the distal direction during curving, thereby further reducing the risk that the distal-end tip 40 will break apart from the distal end of the inner shaft 50.

Figure 4:
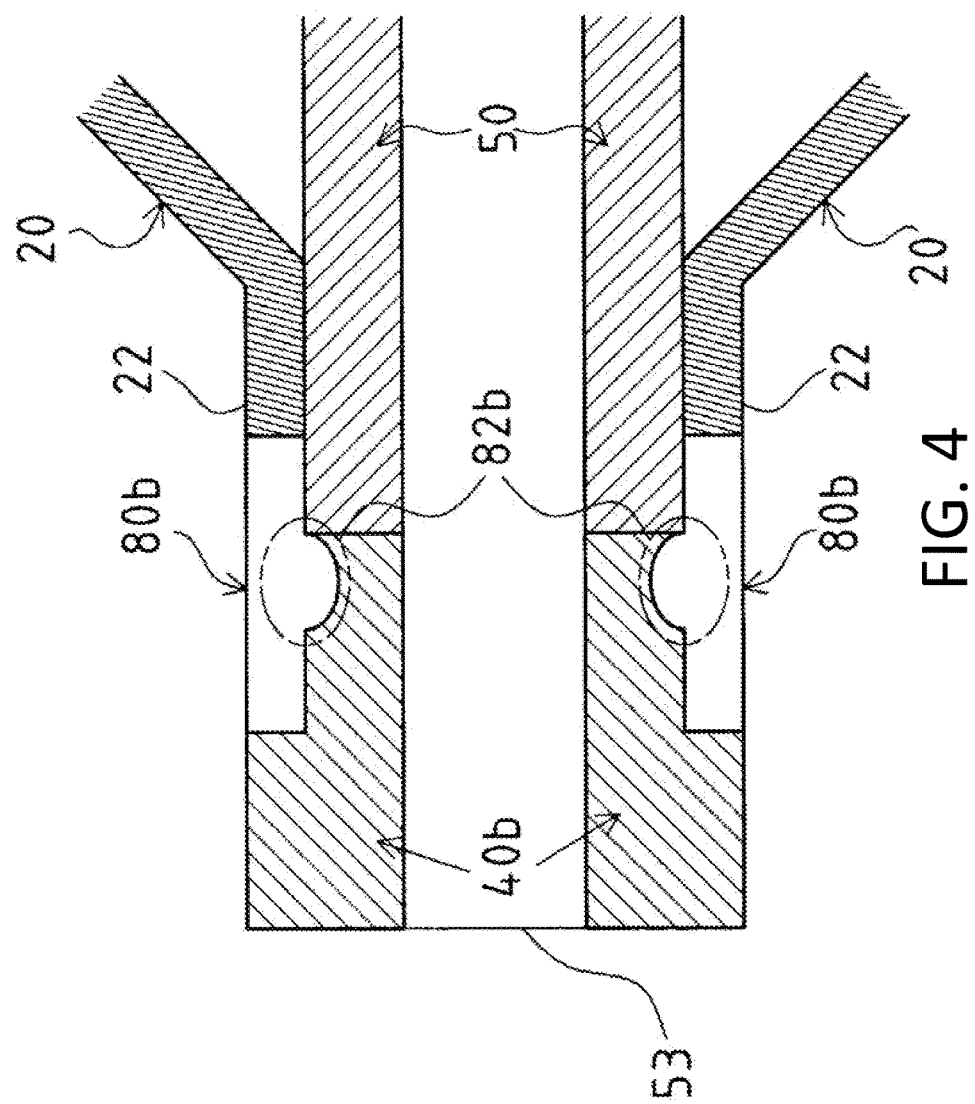
FIG. 4 shows a modification of FIG. 2A, in which the thick portion of a connecting tube is in contact with the distal end of the inner shaft.

FIG. 4 shows that a thick portion 82b of a connecting tube 80b is in contact with the distal end of the inner shaft 50. Because the thick portion 82b is in contact with the distal end of the inner shaft 50, a pressing force applied by an operator in the distal direction of the balloon catheter 10 can be gradually transmitted from the inner shaft 50 to the distal-end tip 40b through the thick portion 82b of the connecting tube 80b. Particularly when the connecting tube 80b is made of a resin having a greater stiffness than the distal-end tip 40b and a lower stiffness than the inner shaft 50, and the thick portion 82b is in contact with the distal end of the inner shaft 50, the pressing force applied by the operator is easily transmitted between the distal end of the inner shaft 50 and the proximal end of the distal-end tip 40b without loss of the pressing force at the boundary 90. This can improve the operability of the balloon catheter 10 for an operator.

Figure 5:
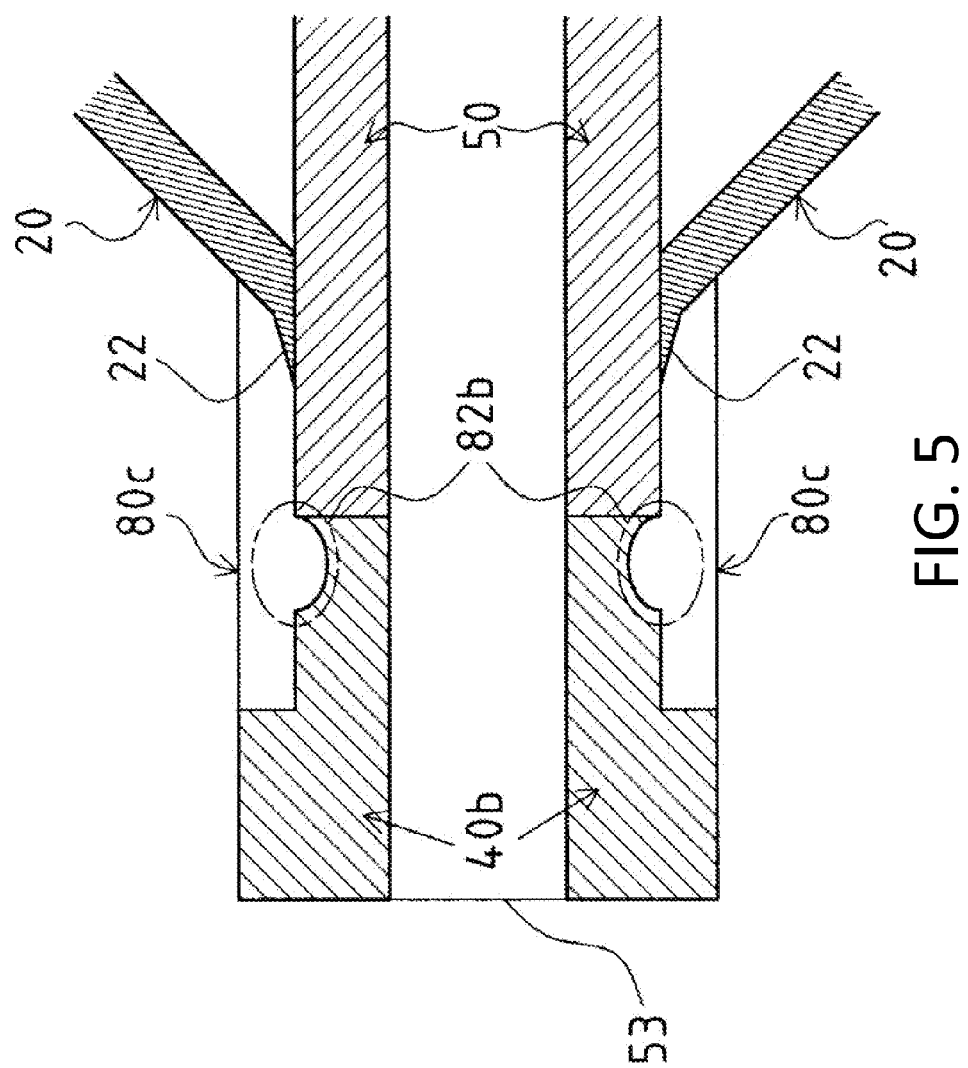
FIG. 5 shows a modification of FIG. 2A, in which the proximal end of the connecting tube extends to and covers the distal end of the balloon.

In FIG. 5, the proximal end of a connecting tube 80c extends to the distal-end attachment part 22 of the balloon 20 so as to cover the distal end of the inner shaft 50 and the distal-end attachment part 22 of the balloon 20. Because the connecting tube 80c covers the distal-end attachment part 22 of the balloon 20, it is less likely that the balloon 20 will detach from the inner shaft 50 when a liquid passes through the balloon 20 at a high pressure.

The shapes of the distal-end tips 40, 40a, 40b, 40c, and 40d are not limited to those of FIGS. 1 to 6B. The distal-end tip may be tapered with an outside diameter decreasing toward the distal end. In FIGS. 1 to 6B, for simplification, the connecting tubes 80, 80a, 80b, 80c, 100, and 110 have a constant thickness in the longitudinal direction except for at the thick portions 82, 82a, 82b, 92, and 102. However, if the connecting tubes 80, 80a, 80b, 80c, 100, and 110 are made of resin having a greater stiffness than the distal-end tips 40, 40a, 40b, 40c, and 40d and a lower stiffness than the inner shaft 50, the connecting tubes 80, 80a, 80b, 80c, 100, and 110 preferably increase in thickness toward the distal direction (except for the thick portions 82, 82a, 82b, 92, and 102). That is, the connecting tubes 80, 80a, 80b, 80c, 100, and 110 are preferably reduced in thickness where covering the outer surface of the inner shaft 50 in order to further reduce the difference in stiffness between the proximal ends of the distal-end tips 40, 40a, 40b, 40c, and 40d and the distal end of the inner shaft 50; meanwhile, the connecting tubes 80, 80a, 80b, 80c, 100, and 110 are preferably increased in thickness where covering the outer surfaces of the distal-end tips 40, 40a, 40b, 40c, and 40d.

In the balloon catheter 10, the thick portions 82, 82a, 82b, 92, and 102 of the connecting tubes 80, 80a, 80b, 80c, 100, and 110 are embedded into the distal-end tips 40, 40a, 40b, 40c, and 40d. This increases the anchoring effect of the thick portions 82, 82a, 82b, 92, and 102 of the connecting tubes 80, 80a, 80b, 80c, 100, and 110 and welding areas between the outer surfaces of the distal-end tip 40, 40a, 40b, 40c, and 40d and the inner surfaces of the connecting tubes 80, 80a, 80b, 80c, 100, and 110, thereby reducing the risk that the distal-end tips 40, 40a, 40b, 40c, and 40d will break apart from the distal end of the inner shaft 50.

What is claimed is:
1. A balloon catheter comprising:
  a balloon;
  an inner shaft fixed to a distal end of the balloon;
  a distal-end tip fixed to and in direct contact with a distal end of the inner shaft; and a connecting tube covering an outer surface on the distal end of the inner shaft and an outer surface of a proximal end of the distal-end tip, wherein:
the connecting tube has an inwardly protruding portion that is embedded into the distal-end tip, and
a proximal end of the connecting tube is in direct contact with the balloon.

2. The balloon catheter according to claim 1, wherein the connecting tube is made of a resin having a greater stiffness than the distal-end tip and a lower stiffness than the inner shaft.

3. The balloon catheter according to claim 2, wherein the inwardly protruding portion is in contact with the distal end of the inner shaft.

4. The balloon catheter according to claim 2, wherein the proximal end of the connecting tube covers the distal end of the balloon.

5. The balloon catheter according to claim 1, wherein the inwardly protruding portion is in contact with the distal end of the inner shaft.

6. The balloon catheter according to claim 5, wherein the proximal end of the connecting tube covers the distal end of the balloon.

7. The balloon catheter according to claim 1, wherein the proximal end of the connecting tube covers the distal end of the balloon.

8. The balloon catheter according to claim 1, wherein a sum of a thickness of the connecting tube and a thickness of the distal-end tip is constant in a longitudinal direction.

9. The balloon catheter according to claim 1, wherein the inwardly protruding portion protrudes inwardly along an entire circumference of the connecting tube.

10. The balloon catheter according to claim 1, wherein the connecting tube has a plurality of inwardly protruding portions.

11. The balloon catheter according to claim 10, wherein the plurality of inwardly protruding portions is longitudinally provided on the connecting tube.

* * * * *